US00PP12472P2

(12) United States Plant Patent
Cosner et al.

(10) Patent No.: US PP12,472 P2
(45) Date of Patent: Mar. 19, 2002

(54) IMPATIENS PLANT NAMED 'TIPEC'

(76) Inventors: Harlan B. Cosner; Susan L. Cosner, both of P.O. Box 173, Broadbent, OR (US) 97414

( * ) Notice: Subject to any disclaimer, the term of this patent is extended or adjusted under 35 U.S.C. 154(b) by 0 days.

(21) Appl. No.: 09/536,167

(22) Filed: Mar. 23, 2000

(30) Foreign Application Priority Data

Mar. 30, 1999 (CA) ..... 99-1611

(51) Int. Cl.[7] ..... A01H 5/00
(52) U.S. Cl. ..... Plt./317
(58) Field of Search ..... Plt./317, 319

(56) References Cited

U.S. PATENT DOCUMENTS

PP3,921 P * 6/1976 Hope et al. ..... Plt./317

OTHER PUBLICATIONS

UPOV–ROM GTITM Computer Database, 2000/04, GTI Jouve Retrieval Software, citation for 'TiPec'.*

* cited by examiner

*Primary Examiner*—Bruce R. Campell
*Assistant Examiner*—Susan B. McCormick
(74) *Attorney, Agent, or Firm*—Bradley M. Ganz, Esq.

(57) ABSTRACT

A new and distinct cultivar of *Impatiens walleriana* plant named 'TiPec' characterized by large peach-colored fully double flowers, flowers that are positioned above or beyond the foliage, dark green foliage and mounded, freely branching and dense plant habit.

1 Drawing Sheet

BACKGROUND—FIELD OF INVENTION

The present invention relates to a new and distinct cultivar botanically known as *Impatiens walleriana*, and by the cultivar name 'TiPec'.

The cultivar of the photograph was developed and selected in a controlled breeding program in a controlled environment in Coquille, Oreg. by the inventors, Harlan Cosner and Sue Cosner, as described herein.

BACKGROUND—DESCRIPTION OF THE PRIOR ART

The closest known cultivar of prior art is named '*Tioga Peach*', subject of U.S. Plant Pat. No. 10,032.

COMPARISON

The impatiens plant of the present invention differs from prior plants, namely '*Tioga Peach*' in at least the following ways:

1. The plant of the present invention has been shown to branch better; and

2. The flowers of the present invention open better, '*Tioga Peach*' had a tendency to have only partially opened flowers;

These and other characteristics will be apparent to persons skilled in the art.

BACKGROUND—DISCOVERY

The present cultivar was developed by standard cross-pollination. Its seed parent is a semi-double impatiens plant with light salmon-colored flowers. This plant was designated B-9X-3109 under the inventors' controlled breeding program. The pollen parent is a pollen-producing double impatiens plant with dark salmon-colored flowers. This plant was designated B-9X-1318 under the inventors' controlled breeding program. The parent plants are not the subject of any granted patent or pending application. The cross was made in the inventors' controlled breeding program, and the first asexual reproduction was made at Broadbent, Oreg. Successive asexually reproduced generations have shown the present invention to be stable. Each asexually reproduced generation has been accomplished using lateral stems with leaves.

The traits of the cultivar of the present invention that have been observed in each successive generation of asexual reproduction, and which are unique are the large peach-colored fully double flowers, flowers that are positioned above or beyond the foliage, dark green foliage and mounded, freely branching and dense plant habit.

Color references are according to The Royal Horticultural Society Colour Chart, except where general terms of ordinary dictionary significance are used.

DETAILED DESCRIPTION

The following observations, measurements and description of the plants and flowers are based on the environmental and cultural practices at Broadbent, Oreg. The following measurements, values and comparisons describe plants grown under a double layer of polyethylene film with temperatures typically ranging from about 55° F. to about 85° F. during the daytime. Night heat was provided by bench top set at 62° F. The individual plants were grown in six-inch Azalea containers in a soiless medium. Plants were liquid fed with high nitrate plus trace elements applied at N level 150 PPM of two successive feedings followed by one leaching with clear water. Plants started in the last week of August and finished in early December and were grown under light levels of 4,000 to 6,000 ft. candles, the description was taken at light levels of 780 ft. candles.

The plant of the present invention has not been observed in all possible environmental and/or cultural conditions. The phenotype may vary significantly with variations in environment such as temperature, light level, humidity and also with cultural practices such as fertility, soil and water quality.

The accompanying photograph illustrates the overall appearance and the flower color of the cultivar of the present invention described herein. The photograph was taken of a mature plant 14 weeks of age during full inflorescence. There may be variations between the colors in the photograph and the colors in the following description due to, for example, light reflectance, or the amount of blue or red light captured in the film. If such variations occur, the written description shall control.

Parentage: The new cultivar was developed by standard cross-pollination. As noted above, its seed parent was a semi-double with light salmon flowers; its pollen parent was a pollen-producing double with dark salmon flowers.

Propagation:

*Type cutting*.—Lateral stems with leaves were the cuttings used for asexual reproduction.

*Time to initate roots*.—Approximately 7 to 14 days at 72° F. soil temperature.

Appearance and form of plant:

*Plant form and habit*.—Mounded to slightly upright, with a medium vigorous, dense and bushy growing habit. A free-branching habit.

*Plant size*.—Height is about 24 cm, and width is about 30 cm.

*Root description*.—The rooting habit is characterized by numerous, fibrous and well-branched roots.

*Branching habit*.—Plants are self-branching. Stems are strong and freely produced. The number of stems depends upon cultural practices, age of stems used as cuttings and the number of growth buds present on the cutting when stuck. The observed plant's average stem length is about 22.5 cm. Each stem generally produces about three laterals.

*Stems*.—Length of stems varies with age and cultural practices. Diameter is about 0.5 cm, internode length is about 2.5 cm. Color is 146C on newer growth, developing dark spots or streaks with age, the color of which is hard to determine due to their small size, but which appear close to either 178A to 178B, these spots or streaks appear in the greatest numbers at the node regions. The observed plant's stem texture is smooth.

*Foliage*.—Leaves are simple, generally symmetrical, abundant, alternate and flat. Shape is ovate, with acuminate apex, attenuate base, and crenate margin. The texture is satiny and smooth. The observed plant's leaf venation pattern is similar to other plants having similar leaf shapes, with single veins branching upwardly off from the central, longitudinal axis of each leaf, along the length of the axis, toward the margin of the leaf and forming an acute angle relative to the axis.

*Foliage size*.—Size of the largest leaves is about 6 cm in length, and 3.7 cm in width.

*Foliage color*.—Adaxial surface color is darker than 147A, venation is 148B. Abaxial surface is close to 148B with dark markings which appear closest to 178A with a greenish overtone that makes them hard to determine with precision, venation is 146B.

*Petioles*.—Each petiole is half round with a flat upper surface. The largest have a width of about 2 mm, a depth of about 2 mm, and a length of about 4 cm. Adaxial surface color is close to 194C, Abaxial surface is close to 194C, both adaxial and abaxial surfaces have an undeterminable reddish tinge over the above described colors.

*Flower size*.—The largest flowers have a diameter of about 4.5 cm, a depth of about 2 cm and a petal count of generally 25 or more.

*Flower texture*.—The flower texture is smooth and satiny.

*Flower count*.—12 to 15 flowers per branch at any time during the flowering season (count includes visible buds to mature, fully open flowers).

*Flower fragrance*.—No discernible fragrance.

*Natural flowering season*.—Year around under greenhouse conditions, and the frost-free period from spring through fall outdoors.

*Duration of flowering*.—Continuous throughout the flowering season.

*Time to flower*.—About six weeks from a rooted cutting.

*Buds*.—Buds are ovate in shape with a length of about 0.8 cm, a width of about 0.7 cm and a depth of about 0.8 cm. Tops of the buds are closest to 142B, Bottoms of buds are 142D.

*Petal size and shape*.—Largest petals consist of two fused at the base. Length of each is about 2 cm and width is about 2 cm. Shape is exaggerated obovate (closer to the reverse of deltoid), cuneate to obtuse base, entire margin, obtuse to retuse apex.

*Petal color*.—Adaxial surface is 49A with a stripe of close to 76D near base between main 49A color and a purplish base spot of 74A to 74D. Abaxial surface is 49B with a whitish stripe close to 76D toward base, between main 49B coloring and a base spot of 74D to 66D.

*Petal count*.—Numerous, generally 20 or more the largest flowers as stated above generally have 25 or more petals.

*Spur*.—There may be from 1 to 3 spurs each described as follows; shape is a curved acicular tube about 2.5 cm in length, when spur is single it may be up to 3.5 cm in length. Sepal end width is about 2 mm. Color is 165B with an apical spot close to 171A.

*Calyx*.—The calyx consists of a single sepal. There is one sepal that is usually so deformed it cannot be described, it usually dries up soon after the flower opens. The following description is the closest approximation the inventors could determine. Length of about 1 cm and a width of about 0.8 cm. Color of adaxial surface is 145D with a basal circle at point of spur attachment close to 74B. Abaxial surface color is 145C with a base circle of close to 74C to 74D with a greenish overtone, Shape is narrow deltoid with entire margin, cordate base, cuspidate apex.

*Peduncles*.—Length is about 2.6 cm and diameter is about 2 mm. Color is 146C, with a moderate strength. Peduncles have a smooth texture.

*Pedicels*.—Usually two to four. Length is about 2.25 cm and diameter is about 1.5 mm. Color is 146C with a moderate strength. Pedicels have a smooth texture.

*Reproductive organs*.—The plants of the new cultivar are both male and female sterile. No reproductive organs have been found to exist.

*Disease resistance*.—Plants have shown to have fair resistance to botrytis.

*Rooting ability*.—Easy, no hormones are needed.

What is claimed:

1. A new and distinct cultivar of *Impatiens walleriana* plant as illustrated and as described herein.

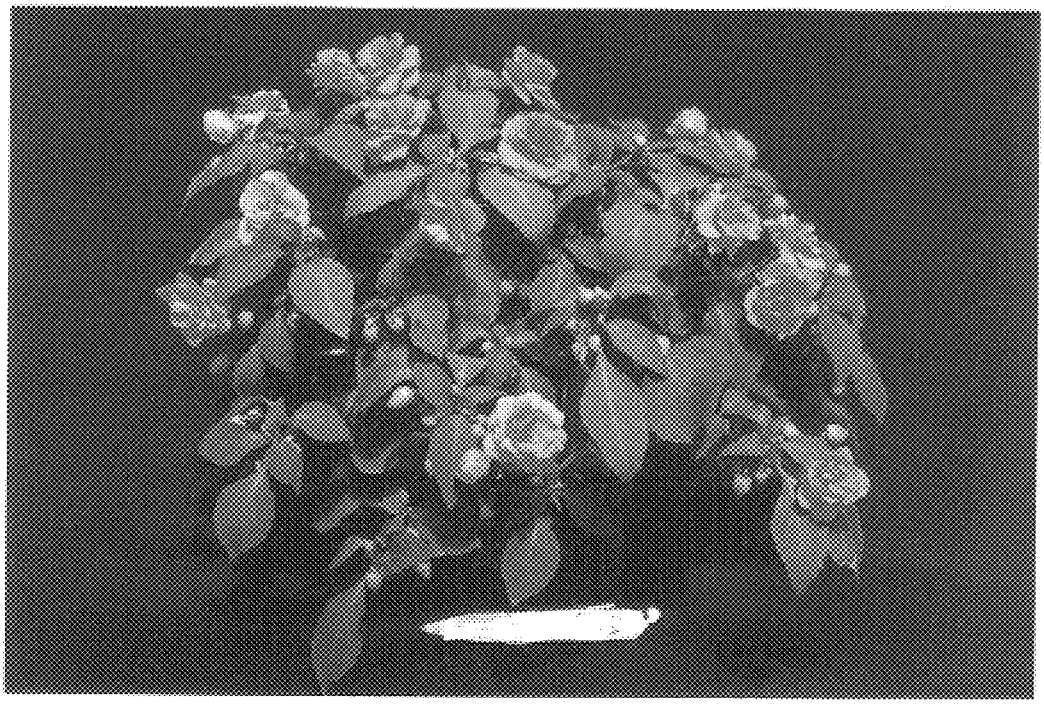

* * * * *